United States Patent
Konishi et al.

(10) Patent No.: US 9,956,159 B2
(45) Date of Patent: May 1, 2018

(54) OIL-BASED COSMETIC

(71) Applicant: SHIN-ETSU CHEMICAL CO., LTD., Tokyo (JP)

(72) Inventors: Masayuki Konishi, Tokyo (JP); Chihiro Hayakawa, Tokyo (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 59 days.

(21) Appl. No.: 14/889,630

(22) PCT Filed: May 1, 2014

(86) PCT No.: PCT/JP2014/062045
§ 371 (c)(1),
(2) Date: Nov. 6, 2015

(87) PCT Pub. No.: WO2014/185275
PCT Pub. Date: Nov. 20, 2014

(65) Prior Publication Data
US 2016/0081904 A1 Mar. 24, 2016

(30) Foreign Application Priority Data

May 13, 2013 (JP) ................................ 2013-100931

(51) Int. Cl.
| A61K 8/73 | (2006.01) |
| A61K 8/37 | (2006.01) |
| A61Q 1/00 | (2006.01) |
| A61Q 1/10 | (2006.01) |
| A61K 8/26 | (2006.01) |
| A61K 8/41 | (2006.01) |
| A61K 8/92 | (2006.01) |
| A61K 8/58 | (2006.01) |

(52) U.S. Cl.
CPC ................ *A61K 8/73* (2013.01); *A61K 8/26* (2013.01); *A61K 8/37* (2013.01); *A61K 8/416* (2013.01); *A61K 8/585* (2013.01); *A61K 8/92* (2013.01); *A61Q 1/00* (2013.01); *A61Q 1/10* (2013.01); *A61K 2800/591* (2013.01)

(58) Field of Classification Search
None
See application file for complete search history.

(56) References Cited

U.S. PATENT DOCUMENTS

| 6,248,336 B1 * | 6/2001 | McDermott | A61K 8/04 424/401 |
| 6,264,933 B1 * | 7/2001 | Bodelin | A61K 8/044 424/401 |
| 6,726,917 B2 | 4/2004 | Kanji et al. | |
| 2005/0276779 A1 * | 12/2005 | Blin | A61K 8/891 424/70.16 |
| 2009/0035237 A1 * | 2/2009 | Maes | A61K 8/06 424/59 |
| 2010/0034880 A1 * | 2/2010 | Sintov | A61K 9/0014 424/484 |
| 2010/0260698 A1 * | 10/2010 | Galante | A61K 8/046 424/65 |

FOREIGN PATENT DOCUMENTS

| CN | 1189093 A | 7/1998 |
| JP | 63-96114 A | 4/1988 |
| JP | 2004-517092 A | 6/2004 |
| JP | 206-213679 A | 8/2006 |
| JP | 2007-314655 A | 12/2007 |
| JP | 2007314655 | * 12/2007 |
| JP | 2008-105994 A | 5/2008 |
| JP | 2012-188394 A | 10/2012 |
| JP | 2013-79211 A | 5/2013 |

OTHER PUBLICATIONS

International Search Report, issued in PCT/JP2014/062045, dated Jun. 3, 2014.
Written Opinion of the International Searching Authority, issued in PCT/JP2014/062045, dated Jun. 3, 2014.
Extended European Search Report issued in Application No. 14798131.0 dated Sep. 21, 2016.
Mintel, "Mascara Integral," Feb. 2010, XP-002761433, Database Accession No. 1265712, 3 pages.
Chinese Office Action and Search Report, dated Apr. 26, 2017, for Chinese Application No. 201480026099.0, with an English translation of the Office Action.

* cited by examiner

*Primary Examiner* — Jennifer A Berrios

(74) *Attorney, Agent, or Firm* — Birch, Stewart, Kolasch & Birch, LLP

(57) ABSTRACT

Provided is an oil-based cosmetic comprising a siliconized polysaccharide compound, silicone emulsifier, organic modified clay mineral, carbonic acid ester, and wax. According to the present invention, a spinnable oil-based composition having exceedingly excellent adherability can be obtained by using a specific siliconized polysaccharide compound, silicone emulsifier, organic modified clay mineral, carbon dioxide ester, and wax, and if this composition is used in an eyelash cosmetic material, it is possible to obtain an eyelash cosmetic material that has excellent adherability, has an excellent long-lash effect without adding fibers, and is capable of imparting a natural finished look.

15 Claims, No Drawings

OIL-BASED COSMETIC

TECHNICAL FIELD

The present invention relates to an oil-based cosmetic preparation formulated with, as a thickening agent, a silicone-modified polysaccharide compound, which preparation has stringiness and is pleasant to use. The invention relates more particularly to an oil-based cosmetic preparation for hair which is useful as an eyelash cosmetic (such as mascara).

BACKGROUND ART

Because they are useful in various ways, compositions having stringiness are being studied in a variety of fields, including not only cosmetics and quasi-drugs, but also foods and resins. Stringiness refers to the quality that a highly viscous liquid has of forming a string when allowed to drip down or when a rod is inserted into the liquid and then quickly drawn up out of the liquid. In order for this quality to be employed in various applications, a composition is required to have a stringiness and viscosity that are suitable for the intended purpose.

One application for stringy compositions is hair cosmetics, especially cosmetics for eyelashes. Eyelash cosmetics are used because they make the eyelashes look long and beautiful, and thus have the effect of highlighting the eyes. To address this aim, there exists art which imparts a long-lash effect and a volume-adding effect by formulating a stringy composition. Specifically, there exists art which, by including both a lysine derivative-modified silicone and a silicone-modified polysaccharide compound, imparts stringiness and extends the length of the eyelashes (see, for example, Patent Document 1: JP-A 2007-314655). At the same time, art has been disclosed wherein both fibers and an adhesive film-forming agent are included in an eyelash cosmetic which, by applying fibers to the eyelashes, adds volume to the eyelashes (see, for example, Patent Document 2: JP-A 2004-517092). There is also art on oil-based gelling agents composed of a siliconized polysaccharide and a polyether-modified silicone (see, for example, Patent Document 3: JP-A 2008-105994).

However, although eyelash cosmetics which include fibers have a good long-lash effect, applying too much fiber to the eyelashes results in an unnatural finish. Also, even though waxes such as beeswax are included in eyelash cosmetics so as to impart adherence and volume, sufficient viscosity is not obtained with an oil-based gelling agent composed of a silicone-modified polysaccharide compound and a polyether-modified silicone, making it inadequate as a gelling agent for eyelash cosmetics.

PRIOR ART DOCUMENTS

Patent Documents

Patent Document 1: JP-A 2007-314655
Patent Document 2: JP-A 2004-517092
Patent Document 3: JP-A 2008-105994

SUMMARY OF THE INVENTION

Problems to be Solved by the Invention

This invention has been done in view of the above circumstances. It is therefore an object of this invention to provide an oil-based cosmetic which has excellent adherence and, particularly when used on eyelashes, has an excellent eyelash-extending effect even if not formulated with fibers and is thus able to impart a naturally looking finish.

Means for Solving the Problems

As a result of extensive investigations, the inventors have discovered that, by using a silicone-modified polysaccharide compound, a silicone emulsifier, an organic-modified clay mineral, a carbonate ester and a wax as the ingredients for an oil-based cosmetic preparation, there can be obtained a stringy oil-based composition of excellent adherence which, when used as an eyelash cosmetic, has an excellent adherence and moreover has a long-lash effect and a natural looking finish that are outstanding.

Accordingly, the invention provides the following oil-based cosmetic preparation.

[1] An oil-based cosmetic preparation comprising a silicone-modified polysaccharide compound, a silicone emulsifier, an organic-modified clay mineral, a carbonate ester and a wax.

[2] The oil-based cosmetic preparation according to [1] which is characterized in that the silicone emulsifier is one, two or more selected from among polyoxyalkylene-modified silicones and polyglycerol-modified silicones.

[3] The oil-based cosmetic preparation according to [1] or [2], wherein the silicone-modified polysaccharide compound is a compound of the general formula (1) below:

[Chemical Formula 1]

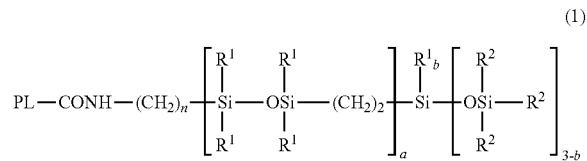

wherein PL is a glucose residue of pullulan; $R^1$ is identical or different and an unsubstituted or substituted monovalent hydrocarbon group of 1 to 10 carbon atoms; $R^2$ is identical or different and an unsubstituted or substituted monovalent hydrocarbon group of 1 to 10 carbon atoms or a siloxy group of the formula $-OSi(R^3)_3$; $R^3$ is identical or different and an unsubstituted or substituted monovalent hydrocarbon group of 1 to 8 carbon atoms; "n" is an integer from 1 to 10, "a" is 0 or 1, and "b" is 0, 1 or 2; and the average bonding number or degree of substitution of silicone compound per constituent sugar unit on the polysaccharide compound is from 0.5 to 2.5, and wherein the silicone-modified polysaccharide compound has an average molecular weight of from 50,000 to 10,000,000.

[4] The oil-based cosmetic preparation according to [3], wherein the silicone-modified polysaccharide compound is siliconized pullulan of the general formula (5) below:

[Chemical Formula 2]

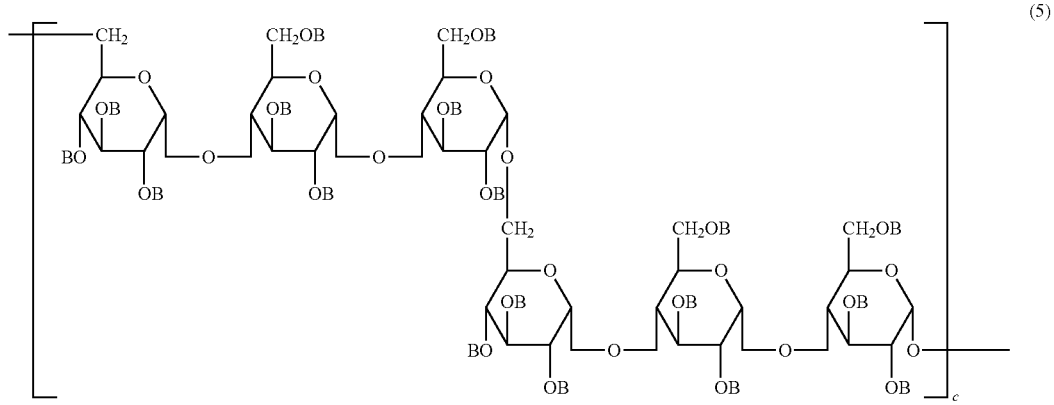

wherein B is a hydrogen atom or —CONH(CH$_2$)$_3$Si[OSi(CH$_3$)$_3$]$_3$, the degree of substitution is from 0.5 to 2.5, and "c" is a number from 100 to 20,000.

[5] The oil-based cosmetic preparation according to any one of [1] to [4], wherein the organic-modified clay mineral is dimethyldistearylammonium hectorite, dimethyldistearylammonium bentonite or dimethyldistearylammonium-modified montmorillonite.

[6] The oil-based cosmetic preparation according to any one of [1] to [5], wherein the amount of silicone-modified polysaccharide compound is from 0.5 to 6 wt %, the amount of silicone emulsifier is from 0.5 to 10 wt %, the amount of organic-modified clay mineral is from 2 to 10 wt %, the amount of carbonate ester is from 0.5 to 10 wt %, and the amount of wax is from 3 to 20 wt %.

[7] The oil-based cosmetic preparation according to any one of [1] to [6], further comprising a volatile oil.

[8] The oil-based cosmetic preparation according to any one of [1] to [7] for use on hair.

[9] The oil-based cosmetic preparation according to [8] for use on eyelashes.

Advantageous Effects of the Invention

According to this invention, by using a specific siliconized polysaccharide, silicone emulsifier, organic-modified clay mineral, carbonate ester and wax, a stringy oil-based composition of truly outstanding adherence can be obtained. When this composition is used in cosmetic preparations for eyelashes, it is possible to obtain eyelash cosmetics which have an excellent adherence, provide an excellent long-lash effect even when not formulated with fibers, and are capable of imparting a natural-looking finish.

EMBODIMENT FOR CARRYING OUT THE INVENTION

An embodiment of the invention is described in detail below, although the invention is not in any way limited thereby.

In this invention, "oil-based cosmetic preparation" refers to a cosmetic preparation in which the continuous phase is oil-based, and includes nonaqueous cosmetic preparations and water-in-oil emulsified cosmetic preparations. Also, "hair cosmetic" refers to a cosmetic preparation for use on human hair, such as the hair on the crown of the head, the eyebrows and the eyelashes.

[Silicone-Modified Polysaccharide Compound]

The silicone-modified polysaccharide compound used in the invention is preferably one of the general formula (1) below.

[Chemical Formula 3]

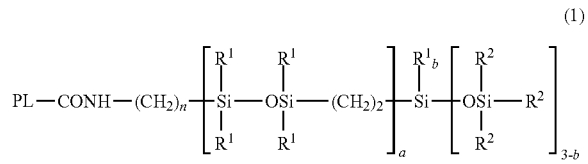

In formula (1), PL is a glucose residue of pullulan; R$^1$ is identical or different and an unsubstituted or substituted monovalent hydrocarbon group of 1 to 10 carbon atoms; and R$^2$ is identical or different and an unsubstituted or substituted monovalent hydrocarbon group of 1 to 10 carbon atoms or a siloxy group of the formula —OSi(R$^3$)$_3$; R$^3$ is identical or different and an unsubstituted or substituted monovalent hydrocarbon group of 1 to 8 carbon atoms. Also, "n" is an integer from 1 to 10, "a" is 0 or 1, and "b" is 0, 1 or 2. The average bonding number (or degree of substitution) of silicone compound per constituent sugar unit on the polysaccharide compound is from 0.5 to 2.5. This silicone-modified polysaccharide compound has an average molecular weight of from 50,000 to 10,000,000.

Here, in general formula (1), PL is a glucose residue of pullulan.

R$^1$ is identical or different and an unsubstituted or substituted monovalent hydrocarbon group of 1 to 10 carbon atoms, preferably 1 to 8 carbon atoms. R$^2$ is identical or different and an unsubstituted or substituted monovalent hydrocarbon group of 1 to 10 carbon atoms, preferably 1 to 8 carbon atoms, or a siloxy group of the formula —OSi(R$^3$)$_3$, with R$^3$ is identical or different and an unsubstituted or substituted monovalent hydrocarbon group of 1 to 8 carbon atoms, preferably 1 to 6 carbon atoms. Illustrative examples of these unsubstituted or substituted monovalent hydrocarbon groups R$^1$ to R$^3$ include alkyl groups such as methyl, ethyl, propyl, isopropyl, butyl, isobutyl, tert-butyl, pentyl, hexyl, cyclohexyl, heptyl and octyl groups; alkenyl groups such as vinyl and allyl groups; aryl groups such as phenyl groups; and aralkyl groups such as benzyl groups; as well as any of these groups in which some or all of the hydrogen atoms have been substituted with, for example, halogen atoms such as fluorine, bromine or chlorine, or cyano groups. Examples include chloromethyl, chloropropyl, bromoethyl, trifluoropropyl and cyanoethyl groups. In terms of, for example, ease of synthesis and stability of the compound, it is desirable for these unsubstituted or substituted monovalent hydrocarbon groups represented by $R^1$ to $R^3$ to be preferably unsubstituted or halogen-substituted monovalent hydrocarbon groups, especially unsubstituted monovalent hydrocarbon groups, and more preferably alkyl groups or aryl groups, especially methyl, ethyl or phenyl groups.

Also, "n" is an integer from 1 to 10, and preferably an integer from 1 to 6; "a" is 0 or 1, and preferably 0; and "b" is 0, 1 or 2, and preferably 0.

In the silicone-modified polysaccharide compound of the general formula (1) above, the average bonding number or degree of substitution of silicone compound per constituent sugar unit on the polysaccharide compound (pullulan) is from 0.5 to 2.5, and preferably from 1.0 to 2.0. When the average bonding number is too small, sufficient oil solubility is not obtained; when it is too large, formation of the compound itself becomes difficult. The silicone compound of the general formula (2) below:

[Chemical Formula 4]

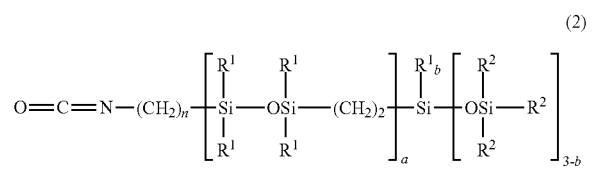

(2)

wherein $R^1$, $R^2$, "n", "a" and "b" are the same as above.

[Chemical Formula 5]

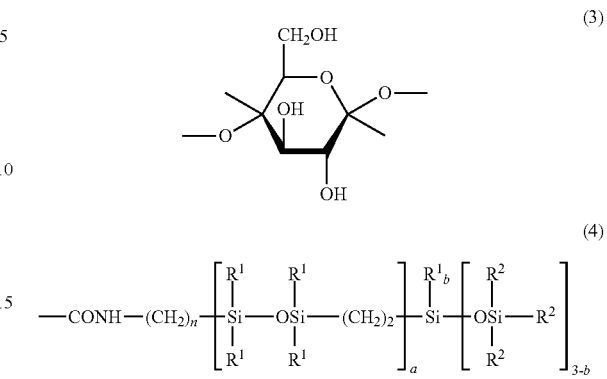

(3)

(4)

wherein $R^1$, $R^2$, "n", "a" and "b" are the same as above.

Also, the silicone-modified polysaccharide compound in this invention has an average molecular weight of from 50,000 to 10,000,000, and preferably from 80,000 to 5,000,000. The average molecular weight can typically be determined as, for example, the polystyrene-equivalent number average molecular weight or weight average molecular weight in gel permeation chromatography analysis using toluene, tetrahydrofuran (THF) as the developing solvent.

In the silicone-modified polysaccharide compound of the invention, it is especially preferable for n=3, a=0, b=0 and $R^2$ to be methyl groups. Examples of such preferred silicone-modified polysaccharide compounds (i.e., cases in which n=3, a=0, b=0, and $R^2$ represents methyl groups) include the siliconized pullulan shown in the general formula (5) below.

[Chemical Formula 6]

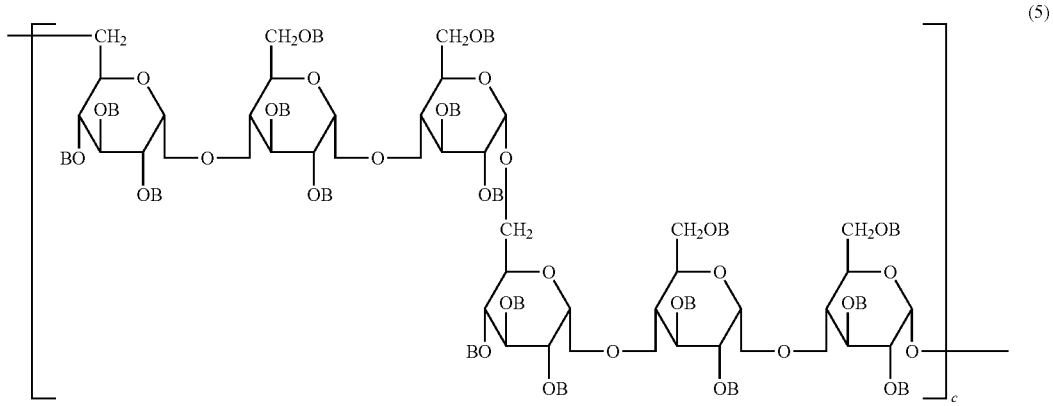

(5)

In this invention, the "degree of substitution of a siliconized polysaccharide" refers to the average bonding number of silicone compound per constituent sugar unit on the polysaccharide compound. For example, the degree of substitution of the silicone-modified polysaccharide compound of the general formula (1) indicates the average number of the substituents shown in the general formula (4) below that are attached to the basic unit of pullulan shown in formula (3) below:

In the general formula (5), B is a hydrogen atom or a group of the formula —$CONH(CH_2)_3Si[OSi(CH_3)_3]_3$, the degree of substitution is from 0.5 to 2.5, and "c" is a number from 100 to 20,000.

The silicone-modified polysaccharide compound of formula (1) above that is used in this invention can be obtained by reacting a terminal isocyanate group-containing silicone compound of the general formula (2) above with a polysaccharide compound (pullulan). A hitherto known method, such as that described in JP-A H08-134103, may be used to carry out such a reaction between a silicone compound and a polysaccharide compound.

The silicone-modified polysaccharide compound used in this invention can be obtained by a known method such as that mentioned above, although use may be made of, specifically, the tri(trimethylsiloxy)silylpropylcarbamoyl pullulan (TSPL) defined in the Japanese Cosmetic Ingredient Labeling Name Dictionary (JCLD), commercial forms of which include TSPL-30-D5, which is TSPL dissolved in decamethylcyclopentasiloxane (available from Shin-Etsu Chemical Co., Ltd.), and TSPL-30-ID, which is TSPL dissolved in isododecane (available from Shin-Etsu Chemical Co., Ltd.).

The amount of silicone-modified polysaccharide compound in this invention, within the overall composition (weight) of the oil-based cosmetic preparation, is from 0.5 to 6 wt %, and preferably from 1.5 to 4 wt %. At less than 0.5 wt %, a sufficient sense of adherence may not be obtained, whereas at more than 6 wt %, the applied film lacks uniformity, as a result of which a natural-looking finish may not be obtained.

[Silicone Emulsifier]

The silicone emulsifier used in the invention is not particularly limited. Use may be made of any silicone emulsifier known to the field of the invention.

Such silicone emulsifiers are exemplified by polyoxyalkylene-modified silicones, polyglycerol-modified silicones and sugar alcohol-modified silicones. In cases where an especially large thickening effect is desired, the use of one, two or more selected from among polyoxyalkylene-modified silicones and polyglycerol-modified silicones is preferred.

Illustrative examples of polyoxyalkylene-modified silicones that may be used include the following defined in the Japanese Cosmetic Ingredient Labeling Name Dictionary (JCLD): PEG-3 Dimethicone, PEG-9 Methyl Ether Dimethicone, PEG-10 Dimethicone, PEG-9 Polydimethylsiloxyethyl Dimethicone, Lauryl PET-9 Polydimethylsiloxyethyl Dimethicone, PEG/PPG-18/18 Dimethicone, Cetyl PEG/PPG-10/1 Dimethicone, Dimethicone/(PEG-10/15) Crosspolymer, PEG-15/Lauryl Dimethicone Crosspolymer, PEG-10/Lauryl Dimethicone Crosspolymer, PEG-15/Lauryl Dimethicone Crosspolymer, and PEG-15/Lauryl Polydimethylsiloxyethyl Dimethicone Crosspolymer. These may be used as mixtures with an optional oil-based ingredient.

Commercial products include the following, available from Shin-Etsu Chemical Co., Ltd.: KF-6015, KF-6016, KF-6017, KF-6028, KF-6028P, KF-6038, KSG-210, KSG-240, KSG-310, KSG-320, KSG-330, KSG-340, KSG-320Z and KSG-350Z.

Illustrative examples of polyglycerol-modified silicones that may be used include the following defined in the Japanese Cosmetic Ingredient Labeling Name Dictionary (JCLD): Polyglyceryl-3 Polydimethylsiloxyethyl Dimethicone, Lauryl Polyglyceryl-3 Polydimethylsiloxyethyl Dimethicone, Bis-Butyl Dimethicone Polyglyceryl-3, Dimethicone/Polyglycerin-3 Crosspolymer, Lauryl Dimethicone/Polyglycerin-3 Crosspolymer and Polyglyceryl-3/Lauryl Polydimethylsiloxyethyl Dimethicone Crosspolymer. These may be used as mixtures with an optional oil-based ingredient.

Commercial products include the following, available from Shin-Etsu Chemical Co., Ltd.: KF-6104, KF-6105, KF-6109, KSG-710, KSG-810, KSG-820, KSG-830, KSG-840, KSG-820Z and KSG-850Z.

The amount of silicone emulsifier in this invention, within the overall composition (weight) of the oil-based cosmetic preparation, is from 0.5 to 10 wt %, and preferably from 1.5 to 3 wt %. At less than 0.5 wt %, a sufficient sense of adherence may not be obtained, whereas at more than 10 wt %, the applied film lacks uniformity, as a result of which a natural-looking finish may not be obtained.

[Organic-Modified Clay Mineral]

The organic-modified clay mineral used in this invention is not particularly limited, provided it is a material that can generally be included in cosmetic preparations. Preferred examples include dimethyldistearylammonium hectorite, dimethyldistearylammonium bentonite and dimethyldistearylammonium-modified montmorillonite. Examples of such materials include BENTONE 38 V CG (dimethyldistearylammonium hectorite) and BENTONE 34 (dimethyldistearylammonium bentonite), both available from Elementis Specialties. One, two or more of these organic-modified clay minerals may be used.

The synthetic organic-modified bentonite that is added may even be one which is pre-swollen with oil. Examples of such materials include BENTONE GEL ISD V, BENTONE GEL MIO V and BENTONE GEL VS-5 V, all available from Elementis Specialties, any of which may be used.

The amount of organic-modified clay mineral in the invention, within the overall composition (weight) of the oil-based cosmetic preparation, is from 2 to 10 wt %, and preferably from 3 to 6 wt %. At less than 2 wt %, a sufficient sense of adherence may not be obtained, whereas at more than 10 wt %, the applied film lacks uniformity, as a result of which a natural looking finish may not be obtained.

[Carbonate Ester]

The carbonate ester used in this invention is not particularly limited, provided it is a raw material that can generally be included in cosmetic preparations, and may be a cyclic carbonate ester or a ring-opened carbonate ester. Illustrative examples include ethylene carbonate, dialkyl (C14, 15) carbonates, diethylhexyl carbonate, dicaprylyl carbonate, butylene carbonate and propylene carbonate. Propylene carbonate is preferred. One, two or more of these carbonate esters may be used.

The amount of carbonate ester in the invention, within the overall composition (weight) of the oil-based cosmetic preparation, is from 0.5 to 10 wt %, and preferably from 1 to 3 wt %. At less than 0.5 wt %, a sufficient sense of adherence may not be obtained, whereas at more than 10 wt %, the applied film lacks uniformity, as a result of which a natural-looking finish may not be obtained.

[Wax]

The wax used in the invention is not particularly limited, provided it is a raw material that can generally be included in cosmetic preparations. Specific examples include synthetic hydrocarbon waxes such as ceresin, ozokerite, microcrystalline wax and polyethylene wax; waxes of vegetable origin such as carnauba wax, rice wax, rice bran wax, jojoba wax (including fully hydrogenated jojoba wax) and candelilla wax; and waxes of animal origin such as spermaceti, beeswax and Chinese wax. One, two or more of these waxes may be used.

The amount of wax used in the invention, within the overall composition (weight) of the oil-based cosmetic preparation, is from 3 to 20 wt %, and preferably from 5 to 13 wt %. At less than 3 wt %, a sufficient sense of volume may not be obtained, whereas at more than 20 wt %, the applied film lacks uniformity, as a result of which a beautiful finish may not be obtained.

[Other Ingredients]

A liquid oil component is typically included in the oil-based cosmetic preparation of the invention. There are volatile oils and non-volatile oils. Controlling the volatility is very important from the standpoint of pleasantness of use in eyelash cosmetics. The amount of liquid oil component, within the overall composition (weight) of the oil-based cosmetic preparation, is from 30 to 70 wt %, and preferably form 40 to 65 wt %.

The volatile oils are not particularly limited, provided they are raw materials that can generally be included in cosmetic preparations. Illustrative examples include cyclopentasiloxane, cyclohexasiloxane, methyl trimethicone, isododecane and isohexadecane. Commercial products thereof include the KF-96 series, KF-995 and TMF-1.5, all available from Shin-Etsu Chemical Co., Ltd.

Where necessary, pigments may be included as optional ingredients in the oil-based cosmetic preparation of the invention. The pigments are not particularly limited, provided they can generally be used in makeup cosmetics. Illustrative examples include inorganic pigments such as talc, mica, kaolin, silica, calcium carbonate, zinc white, titanium dioxide, red iron oxide, yellow iron oxide, black iron oxide, ultramarine, Prussian blue, carbon black, lower oxides of titanium, cobalt violet, chromium oxide, chromium hydroxide, cobalt titanate, bismuth oxychloride and titanium-mica pearlescent pigments; organic pigments such as zirconium, barium or aluminum lakes, including Red No. 201, Red No. 202, Red No. 204, Red No. 205, Red No. 220, Red No. 226, Red No. 228, Red No. 405, Orange No. 203, Yellow No. 205, Yellow No. 4, Yellow No. 5, Blue No. 1, Blue No. 404 and Green No. 3; natural colorants such chlorophyll and (3-carotene; and dyes. In addition, pigments that have been rendered hydrophobic with silicone or the like may be used. One, two or more of these pigments may be used.

The amount of pigment is suitably adjusted and, although pigment may or may not be added, when it is added, the amount thereof within the overall composition (weight) of the oil-based cosmetic preparation, is preferably from 0.1 to 30 wt %, and more preferably from 3 to 20 wt %. At less than 0.1 wt %, the pigment effect may be inadequate, whereas an amount of more than 30 wt % may be undesirable from the standpoint of adherence.

In the oil-based cosmetic preparations (for use on hair) according to the invention, such as eyelash cosmetics, if necessary, fibers may be added as an optional ingredient. The fibers are added to impart a long-lash effect that makes the eyelashes appear longer and to form a uniform cosmetic film. Such fibers are not particularly limited, provided they are fibers that are commonly used in cosmetics. Illustrative examples include synthetic fibers such as nylon and polypropylene, manmade fibers such as rayon, natural fibers such as cellulose, and semi-synthetic fibers such as acetate rayon.

Such fibers having a size of 3 to 12 denier (indicated below as simply "D") and a length of 0.1 to 4 mm are more preferred in that they have the effect of making the eyelashes look longer and highlighting the eyes.

The amount of fiber is not particularly limited, although when fiber is added, the amount thereof within the overall composition (weight) of the oil-based cosmetic preparation is preferably from 0.1 to 8 wt %, and more preferably from 0.5 to 5 wt %. One, two or more such types of fiber may be used, and these may be colored black or some other color.

Where necessary, the fibers may be used after being surface-treated. Exemplary finishes for this purpose include fluorine compounds, silicone compounds, powders, oils, gelling agents, polymer emulsions and surfactants. One, two or more types from among these may be used. However, of these, from the standpoint of the effect of making the eyelashes look longer and thus highlighting the eyes, as well as the persistence of this effect, fibers that have been hydrophobically treated with silicone or fluorine are especially preferred.

Microparticulate silica having a high specific surface area (e.g., fine powdery silica such as fumed silica or precipitated silica having a BET specific surface area of at least 50 $m^2/g$, and particularly about 100 to 400 $m^2/g$) is often used for thickening and gelling oil-based cosmetic preparations. Examples of such microparticulate silicas include Aerosil R972 and Aerosil 200, both available from Nippon Aerosil Co., Ltd. However, there are problems with these silicas, including their low apparent specific gravity, which makes them difficult to incorporate. It is possible in this invention to carry out sufficient thickening and gelling even without the addition of such silicas.

EXAMPLES

Working Examples and Comparative Examples are given below to more concretely illustrate the invention, although the invention is not limited by these Examples. Unless noted otherwise, ingredient amounts are indicated in wt %. The test methods used in the invention are described below.
(1) Sensory Evaluation: Stringiness The stringiness when 1 g of a sample containing the above ingredients is applied to the back of a prewashed hand, a finger is pressed against the sample and the finger is then moved upward away from the hand was visually evaluated by an expert panel (10 judges). The rating criteria were set to 5 points when it was felt that the sample extends very well, 3 points when it was felt that the sample extends to some degree, and 1 point when it was felt that the sample does not to extend, and the total score was determined.
  Exc: Total score was 40 points or more
  Fair: Total score was from 21 to 39 points
  NG: Total score was 20 points or less
(2) Application Properties The ease of eyelash cosmetic application when a sample (eyelash cosmetic) is applied to the eyelashes was sensory evaluated by an expert panel (10 judges). The rating criteria were set to 5 points when it was felt that the sample is easy to apply, 3 points when it was felt that the sample is difficult to apply, and 1 point when it was felt that the sample is very difficult to apply, and the total score was determined.
  Exc: Total score was 40 points or more
  Fair: Total score was from 21 to 39 points
  NG: Total score was 20 points or less
(3) Long-Lash Effect An expert panel (10 judges) carried out a sensory evaluation of the long-lash effect in which a sample (eyelash cosmetic) was applied 10 times to the eyelashes and the length of the eyelashes before and after application was visually observed. The rating criteria were set to 5 points when it was felt that the eyelashes had become very long, 3 points when it was felt that the eyelashes had become somewhat longer, and 1 point when there was felt to be no change relative to before application.
  Exc: Total score was 40 points or more
  Fair: Total score was from 21 to 39 points
  NG: Total score was 20 points or less Example 1, Comparative Examples 1 and 2

Oil-based cosmetic preparations were produced according to the formulations shown in Table 1, and their stringiness and thickening properties were evaluated. The results are presented in Table 1.

TABLE 1

| Ingredients (wt %) | Example 1 | Comparative Example 1 | Comparative Example 2 |
|---|---|---|---|
| Silicone-modified polysaccharide compound*[1] | 5 | 5 | 5 |
| Silicone emulsifier*[2] | 10 | 10 | — |
| Organic-modified clay mineral*[3] | 10 | — | 10 |
| Beeswax | 10 | 10 | 10 |
| Propylene carbonate | 10 | — | 10 |
| Isododecane | 55 | 55 | 55 |
| Total | 100 | 80 | 90 |
| Stringiness | good | NG | fair |
| Thickening properties*[4] | good | NG | NG |

*[1]Silicone-modified polysaccharide compound: Tri(trimethylsiloxy)silylpropylcarbamoyl pullulan (TSPL, from Shin-Etsu Chemical Co., Ltd.; degree of substitution in general formula (5), approx. 2.0; molecular weight, approx. 690,000).
*[2]Silicone emulsifier: PEG-9 Polymethylsiloxyethyl Dimethicone (KF-6028P, from Shin-Etsu Chemical Co., Ltd.)
*[3]Organic-modified clay mineral: Quaternium 18-Hectorite (BENTONE 38 V CG, from Elementis Specialties)
*[4]In Table 1, "thickening properties" indicates whether or not there is a distinct thickening effect when compared with a test example. Arbitrarily assigning a rating of "good" to Example 1, cases in which the thickening effect was more distinct than in Example 1 were rated as "Exc," cases in which the thickening effect was comparable with that in Example 1 were rated as "good," and cases in which the thickening effect was clearly inferior to that in Example 1 were rated as "NG." In Comparative Examples 1 and 2, even when 20 wt % and 10 wt %, respectively, of additional isododecane was included to bring the total up to 100 wt %, the results for stringiness and thickening properties were the same as in Comparative Examples 1 and 2 prior to the further addition of isododecane.

In order to control the adherence of an eyelash cosmetic, it is necessary for the cosmetic preparation to be imparted with stringiness and for the viscosity to be controlled. From the results in Table 1, the thickening system in Comparative Example lacked thickening properties. Moreover, as is apparent from Comparative Example 2, one can see that it is not enough to merely add a thickening agent.

Example 2, Comparative Examples 3 to 8

Eyelash cosmetics were prepared according to the formulations shown in Table 2, and the stringiness, application properties and long-lash effect of each were evaluated. The results are presented in Table 2.

Referring to Table 2 above, in Comparative Example 3 which did not include a silicone-modified polysaccharide compound, a thickening effect was obtained and gelling occurred, but the stringiness and the long-lash effect were inadequate. In Comparative Example 4 which did not include a silicone emulsifier, the stringiness and long-lash effect were both weak and a thickening effect was not obtained. In Comparative Example 5 which did not include an organic-modified clay mineral, stringiness was exhibited, but a sufficient thickening effect was not obtained and separation occurred immediately following production. Even in Comparative Example 6 in which another oil-based gelling agent was included as a substitute for an organic-modified clay mineral, somewhat of a thickening effect was obtained, but a tendency for separation similar to that in Comparative Example 5 was observed. In Comparative Example 7 in which wax was not included, no tendency for separation was observed, but a sufficient thickening effect and a long-lash effect were both not obtained. In Comparative Example 8 in which a carbonate ester was not included, a thickening effect was obtained, but the composition separated and a long-lash effect was not obtained.

It is apparent from the above results that, in an eyelash cosmetic according to the invention (Example 2), by using a silicone-modified polysaccharide compound, a silicone emulsifier, an organic-modified clay mineral, a carbonate ester and a wax, the application properties are excellent, a long-lash effect appears and a sufficient thickening effect is obtained.

The invention claimed is:
1. An oil-based cosmetic preparation comprising:
   a silicone-modified polysaccharide compound of general formula (1) below:

TABLE 2

| Ingredients (wt %) | Example 2 | Comparative Example 3 | Comparative Example 4 | Comparative Example 5 | Comparative Example 6 | Comparative Example 7 | Comparative Example 8 |
|---|---|---|---|---|---|---|---|
| Silicone-modified polysaccharide compound*[1] | 4.2 | — | 4.2 | 4.2 | 4.2 | 4.2 | 4.2 |
| Silicone emulsion*[2] | 1.5 | 1.5 | — | 1.5 | 1.5 | 1.5 | 1.5 |
| Organic-modified clay mineral*[3] | 6 | 6 | 6 | — | — | 6 | 6 |
| Dextrin palmitate/2-ethylhexanoate*[5] | — | — | — | — | 6 | — | — |
| Beeswax | 4.5 | 4.5 | 4.5 | 4.5 | 4.5 | — | 4.5 |
| Microcrystalline wax | 8 | 8 | 8 | 8 | 8 | — | 8 |
| Propylene carbonate | 2 | 2 | 2 | 2 | 2 | 2 | — |
| Isododecane | balance | balance | balance | balance | balance | balance | balance |
| Spherical polymethyl silsesquioxane powder*[6] | 5 | 5 | 5 | 5 | 5 | 5 | 5 |
| Acrylic-modified silicone-coated black iron oxide | 5 | 5 | 5 | 5 | 5 | 5 | 5 |
| Acrylic-modified silicone-coated talc | 5 | 5 | 5 | 5 | 5 | 5 | 5 |
| Preservative | 0.2 | 0.2 | 0.2 | 0.2 | 0.2 | 0.2 | 0.2 |
| Total | 100 | 100 | 100 | 100 | 100 | 100 | 100 |
| Stringiness | good | NG | fair | good | good | fair | fair |
| Application properties | good | fair | fair | NG | NG | NG | fair |
| Long-lash effect | good | NG | fair | NG | fair | NG | NG |
| Condition of preparation | gel | gel | cream | separated | separated | fluid | separated |

*[1],*[2],*[3]Same as above
*[5]Dextrin palmitate/2-ethylhexanoate, available as Rheopearl TT from Chiba Flour Milling Co., Ltd.
*[6]Spherical polymethyl silsesquioxane powder (KMP-590, from Shin-Etsu Co., Ltd.)

13

1.

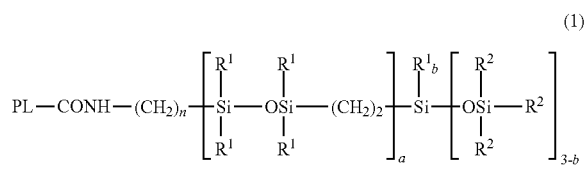

(1)

wherein PL is a glucose residue of pullulan; $R^1$ is identical or different and an unsubstituted or substituted monovalent hydrocarbon group of 1 to 10 carbon atoms; $R^2$ is a methyl group; "n" is 3, "a" is 0, and "b" is 0; and the average bonding number or degree of substitution of silicone compound per constituent sugar unit on the polysaccharide compound is from 0.5 to 2.5, and wherein the silicone-modified polysaccharide compound has an average molecular weight of from 50,000 to 10,000,000;

one or more silicone emulsifiers comprising polyoxyalkylene-modified silicones;

an organic-modified clay mineral, which is dimethyldistearylammonium hectorite, dimethyldistearylammonium bentonite, or dimethyldistearylammonium-modified montmorillonite;

a carbonate ester selected from the group consisting of ethylene carbonate, propylene carbonate, and butylene carbonate; and a wax, wherein the amount of silicone-modified polysaccharide compound is from 0.5 to 6 wt %, the amount of silicone emulsifier is from 0.5 to 10 wt %, the amount of organic-modified clay mineral is from 2 to 10 wt %, the amount of carbonate ester is from 2 to 10 wt %, and the amount of wax is from 3 to 20 wt %.

2. The oil-based cosmetic preparation according to claim 1, wherein the silicone-modified polysaccharide compound is siliconized pullulan of the general formula (5) below:

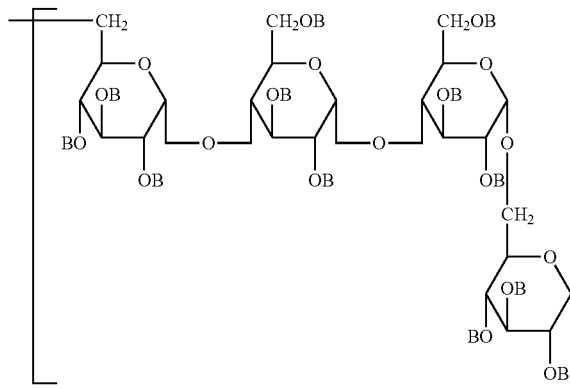

(5)

wherein B is a hydrogen atom or —CONH(CH$_2$)$_3$Si[OSi (CH$_3$)$_3$]$_3$, the degree of substitution of silicone compound per constituent sugar unit on the polysaccharide compound is from 0.5 to 2.5, and "c" is a number from 100 to 20,000.

3. The oil-based cosmetic preparation according to claim 1, wherein the amount of carbonate ester is from 2 to 3 wt %.

4. The oil-based cosmetic preparation according to claim 1, further comprising a volatile oil.

14

5. The oil-based cosmetic preparation according to claim 1 for use on hair.

6. The oil-based cosmetic preparation according to claim 5 for use on eyelashes.

7. The oil-based cosmetic preparation according to claim 1, wherein the silicone emulsifier is PEG-9 polymethylsiloxyethyl dimethicone.

8. The oil-based cosmetic preparation according to claim 1, wherein the organic-modified clay mineral is quaternium 18-hectorite.

9. The oil-based cosmetic preparation according to claim 1, wherein the carbonate ester is propylene carbonate.

10. The oil-based cosmetic preparation according to claim 1, wherein the wax is beeswax.

11. The oil-based cosmetic preparation according to claim 4, wherein the volatile oil is isododecane.

12. An oil-based cosmetic preparation, comprising:
a silicone-modified polysaccharide compound of the general formula (1):

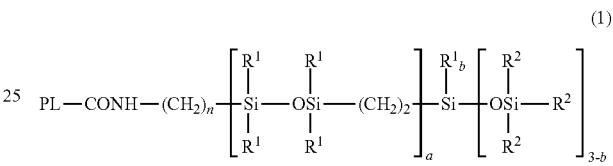

(1)

wherein PL is a glucose residue of pullulan; $R^1$ is identical or different and an unsubstituted or substituted monovalent hydrocarbon group of 1 to 10 carbon atoms; $R^2$ is a methyl group; "n" is 3, "a" is 0, and "b" is 0;
PEG-9 polymethylsiloxyethyl dimethicone;
quaternium 18-hectorite;
propylene carbonate;
beeswax; and
isododecane,

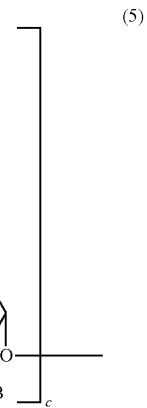

wherein the amount of propylene carbonate is from 2 to 10 wt %; and wherein the amount of silicone-modified polysaccharide compound is from 0.5 to 6 wt %, the amount of PEG-9 polymethylsiloxyethyl dimethicone is from 0.5 to 10 wt %, the amount of quaternium 18-hectorite is from 2 to 10 wt %, the amount of beeswax is from 3 to 20 wt %, and the amount of isododecane is from 30 to 70 wt %.

13. The oil-based cosmetic preparation according to claim 1, wherein the amount of silicone emulsifier is from 1.5 to 10 wt %.

14. The oil-based cosmetic preparation according to claim 4, wherein the amount of volatile oil is from 30 to 70 wt %.

15. An oil-based cosmetic preparation comprising:
a silicone-modified polysaccharide compound of general formula (5):

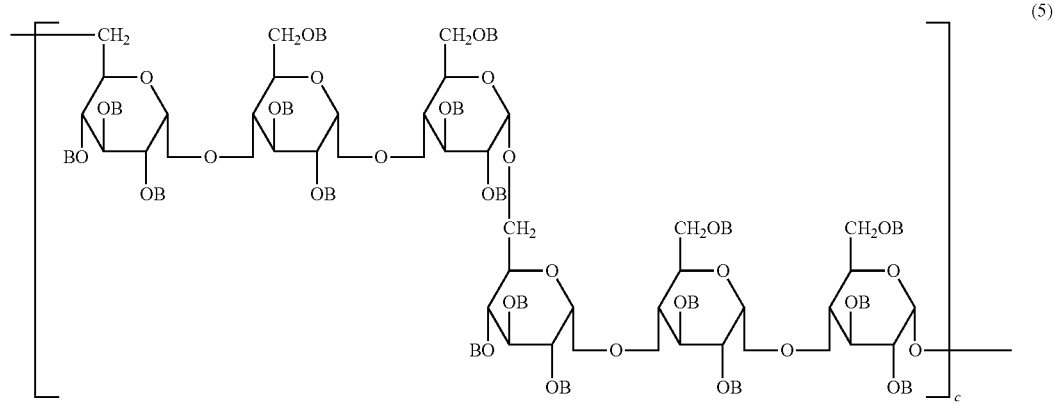

wherein B is a hydrogen atom or —CONH(CH$_2$)$_3$Si[OSi(CH$_3$)$_3$]$_3$, the degree of substitution of silicone compound per constituent sugar unit on the polysaccharide compound is from 0.5 to 2.5, and "c" is a number from 100 to 20,000;
one or more silicone emulsifier comprising polyoxyalkylene-modified silicones;
an organic-modified clay mineral, which is dimethyldistearylammonium hectorite, dimethyldistearylammonium bentonite, or dimethyldistearylammonium-modified montmorillonite,
a carbonate ester selected from the group consisting of ethylene carbonate, propylene carbonate, and butylene carbonate; and
a wax,
wherein the amount of silicone-modified polysaccharide compound is from 0.5 to 6 wt %, the amount of silicone emulsifier is from 0.5 to 10 wt %, the amount of organic-modified clay mineral is from 2 to 10 wt %, the amount of carbonate ester is from 2 to 10 wt %, and the amount of wax is from 3 to 20 wt %.

* * * * *